(12) United States Patent
Redmond et al.

(10) Patent No.: US 10,092,299 B2
(45) Date of Patent: Oct. 9, 2018

(54) DISPOSABLE KERRISON RONGEUR (71) Applicant: Steribite, LLC, Cleveland, OH (US)

(72) Inventors: John A. Redmond, Garrettsville, OH (US); Mark T. Whiteaker, Rocky River, OH (US)

(73) Assignee: STERIBITE, LLC, Cleveland, OH (US)

( * ) Notice: Subject to any disclaimer, the term of this patent is extended or adjusted under 35 U.S.C. 154(b) by 308 days.

(21) Appl. No.: 15/080,883

(22) Filed: Mar. 25, 2016

(65) Prior Publication Data
US 2016/0302801 A1 Oct. 20, 2016

Related U.S. Application Data (60) Provisional application No. 62/148,315, filed on Apr. 16, 2015.

(51) Int. Cl.
*A61B 17/16* (2006.01)
*A61B 17/00* (2006.01)

(52) U.S. Cl.
CPC ... *A61B 17/1611* (2013.01); *A61B 2017/0023* (2013.01); *A61B 2017/00429* (2013.01)

(58) Field of Classification Search
CPC ................................................ A61B 17/1611
See application file for complete search history.

(56) References Cited

U.S. PATENT DOCUMENTS

| 3,093,134 | A | * | 6/1963 | Roehr | A61M 5/343 |
|---|---|---|---|---|---|
| | | | | | 604/272 |
| 3,752,161 | A | | 8/1973 | Bent | |
| 3,902,498 | A | | 9/1975 | Niederer | |
| 4,201,213 | A | * | 5/1980 | Townsend | A61B 17/1611 |
| | | | | | 606/174 |
| 4,722,338 | A | | 2/1988 | Wright et al. | |
| 4,733,663 | A | | 3/1988 | Farley | |
| 4,777,948 | A | | 10/1988 | Wright | |
| 5,026,375 | A | * | 6/1991 | Linovitz | A61B 17/1611 |
| | | | | | 30/349 |

(Continued)

OTHER PUBLICATIONS

Corresponding International Application No. PCT/US2016/027060, International Search Report & Written Opinion dated Jul. 5, 2016.

*Primary Examiner* — Zade Coley
(74) *Attorney, Agent, or Firm* — Cooper Legal Group LLC; Ronald Kachmarik (57) ABSTRACT

A disposable kerrison rongeur. A base includes a handle portion, a body portion and a shaft portion. The shaft portion is made of a metal material and includes a male mold-on interlock portion configured to non-removably interlock with an over-molded plastic material. The body portion is made of plastic material and includes an over-mold interlock portion that is over-molded onto and non-removably fixed onto the mold-on interlock portion of the shaft portion. A slide shaft includes a distal portion and a proximal portion. The distal portion is made of a metal material and includes a male mold-on interlock portion configured to non-removably interlock with an over-molded plastic material. The proximal portion is made of a plastic material and includes an over-mold interlock portion that is over-molded onto and non-removably fixed onto the mold-on interlock portion of the distal portion.

15 Claims, 5 Drawing Sheets

(56) References Cited

U.S. PATENT DOCUMENTS

| | | | |
|---|---|---|---|
| 5,273,519 A | 12/1993 | Koros et al. | |
| 5,385,570 A * | 1/1995 | Chin | A61B 17/1611 600/564 |
| 5,451,227 A | 9/1995 | Michaelson | |
| 5,569,258 A * | 10/1996 | Gambale | A61B 17/1611 606/167 |
| 5,582,618 A | 12/1996 | Chin et al. | |
| 5,766,177 A | 6/1998 | Lucas-Dean et al. | |
| 5,925,050 A | 7/1999 | Howard, III | |
| 6,142,997 A | 11/2000 | Michelson | |
| 6,200,320 B1 * | 3/2001 | Michelson | A61B 10/0096 606/170 |
| 6,575,977 B1 * | 6/2003 | Michelson | A61B 17/1611 606/170 |
| 6,695,849 B2 * | 2/2004 | Michelson | A61B 10/0096 606/170 |
| 7,011,663 B2 * | 3/2006 | Michelson | A61B 10/0096 606/170 |
| 7,297,147 B2 | 11/2007 | Michelson | |
| 7,922,723 B2 * | 4/2011 | Michelson | A61B 17/1611 606/83 |
| 8,241,290 B2 | 8/2012 | Michelson | |
| 9,050,109 B2 * | 6/2015 | Smith | A61B 18/1442 |
| 2002/0049460 A1 * | 4/2002 | Mazur | A61B 17/1606 606/167 |
| 2003/0216740 A1 * | 11/2003 | Michelson | A61B 17/1611 606/83 |
| 2004/0102783 A1 | 5/2004 | Sutterlin, III et al. | |
| 2006/0122615 A1 | 6/2006 | McKinley | |
| 2006/0149271 A1 * | 7/2006 | Michelson | A61B 10/0096 606/83 |
| 2006/0241663 A1 | 10/2006 | Rice et al. | |
| 2013/0041379 A1 * | 2/2013 | Bodor | A61B 17/1611 606/83 |
| 2014/0100593 A1 * | 4/2014 | Sand | A61B 17/1611 606/167 |
| 2014/0257264 A1 * | 9/2014 | Smith | A61B 18/1442 606/33 |
| 2015/0223823 A1 * | 8/2015 | Smith | A61B 18/1442 604/23 |

* cited by examiner

DISPOSABLE KERRISON RONGEUR

RELATED PATENT APPLICATION

This application claims the benefit of priority from U.S. Provisional Patent Application No. 62/148,315 filed Apr. 16, 2015, the contents of which is incorporated herein by reference in entirety.

FIELD OF THE INVENTION

The present invention relates generally to surgical devices. In particular, the present invention relates to kerrison rongeurs.

BACKGROUND

Kerrison rongeurs have been used for many years during spinal and neurological procedures to safely remove tissue, such as bone and or cartilage, near delicate anatomical structures. The design has not changed much over the years, with the exception of surface coatings being applied to increase sharpness longevity. Recently, a "take-apart" kerrison rongeur has been utilized to make cleaning easier and more complete. Even with such a change a number of issues may remain for existing kerrison designs. The follow discussion indicates some example issues.

Reusable kerrison rongeurs are costly to buy and sharpen. Reusable kerrison rongeurs may only be sharpened a limited number of times. Non-ideal handling by surgeons can occur in connection with use of dull kerrison rongeurs. For example, surgeons might twist a dull kerrison and/or rock the dull kerrison up and down to help remove some tissue, such a bone. Such non-ideal handling might lead to bent or broken tips.

Reusable kerrison rongeurs can be difficult to clean properly. Patient blood and bone might be left in channels even after sterilization. It is possible that remaining/remnant blood and/or bone might thus be transferred to a next patient. Even though technically the remaining/remnant blood and/ or bone may be sterile, sterilization may not kill prion type diseases like Creutzfeld-Jakob disease. Creutzfeld-Jakob disease may be incurable. Take-apart kerrison rongeurs can help address some of these issues. However, such an addressing aspect is associated with the hospital personnel and/or others involved in the sterilization process accomplishing a proper and complete disassembly.

Some reusable kerrison rongeurs have footplates that are thick to reduce bending or breaking. This leads to problems for surgeons, who may press the footplate toward/against the spinal cord or nerve root while removing bone leading to post-operative pain and spasms, or more serious issues. Surgeons want the thinnest footplates possible.

Current designs are not comfortable for surgeons to use, and carpel tunnel syndrome could be a problem for busy spine surgeons.

Small screws are used on the shaft and handle to hold them in place, and they can come loose and fall into the operative site.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with an aspect of the present invention, a disposable kerrison rongeur for cutting tissue is provided. The kerrison rongeur includes a base. The base includes a handle portion, a body portion and a shaft portion. The shaft portion has a major elongation along an actuation axis and is made of a metal material. The shaft portion includes a slide support surface that extends along the actuation axis. The shaft portion includes a foot portion that is located at a distal end of the slide support surface and that extends transverse to the actuation axis. The shaft portion includes a male mold-on interlock portion that is located at an end of the shaft portion opposite to the foot portion and that has a contour and geometry configured to non-removably interlock with an over-molded plastic material. The body portion has a major elongation along the actuation axis and is made of the over-molded plastic material. The body portion includes an over-mold interlock portion that is over-molded onto and non-removably fixed onto the mold-on interlock portion of the shaft portion with the plastic material having an internal female contour and geometry that is married to the contour and geometry of the male mold-on interlock portion to be non-removably interlocked with the male mold-on interlock portion of the shaft portion. The body portion includes a slide support surface that extends along the actuation axis. The slide support surface of the body portion is coplanar with the slide surface support of the shaft portion. The body portion includes a lever passageway that extends through the body portion and that has an opening through the slide support surface of the body portion. The body portion includes a bearing bore extending through the body portion on a bore axis. The bearing bore transversely intersecting the lever passageway. The handle portion is made of the over-molded plastic material and extends from the body portion of the base away from the shaft portion of the base and transverse to the actuation axis. The kerrison rongeur includes an operable lever made of a plastic material and moveable relative to the base. The lever includes a pivot portion located within the lever passageway. The pivot portion has a bearing bore that is aligned with the bearing bore of the body portion. The pivot portion is pivotably movable relative to the body portion on the bore axis. The lever includes a handle portion that extends from the pivot portion and away from the body portion transverse to the actuation axis. The handle portion of the lever is movable relative to the handle portion of the base during pivot movement of the pivot portion relative to the body portion. The lever includes an actuator spur that extends from the pivot portion past the opening through the slide support surface of the body portion, away from the body portion and transverse to the actuation axis. The actuator spur is movable relative to the body portion of the base during pivot movement of the pivot portion relative to the body portion. The movement of the actuator spur includes a translational movement component along the actuation axis. The kerrison rongeur includes a slide shaft that has a major elongation along the actuation axis and is moveable relative to the base along the actuation axis. The slide shaft includes a distal portion and a proximal portion. The distal portion is made of a metal material. The distal portion includes a slide surface that extends along the actuation axis and that is supported upon at least the slide support surface of the shaft portion of the base. The slide surface slides upon at least the slide support surface of the shaft portion of the base during movement of the slide shaft relative to the base. The distal portion includes a cutting edge that is located to be opposed to the foot. The cutting edge is movable toward the foot to cut tissue located between the cutting edge and the foot. The distal portion includes a male mold-on interlock portion that is located at an end of the distal portion opposite to the cutting edge and that has a contour and geometry configured to non-removably interlock with an over-molded plastic material. The proximal portion is made of a plastic material. The proximal portion including a slide surface that extends along the actuation axis and supported upon at least the slide support surface of the body portion of the base. The slide surface of the proximal portion of the slide shaft slides upon at least the slide support surface of the body portion of the base during movement of the slide shaft relative to the base. The proximal portion includes an actuator spur receptacle extending into the proximal portion from the slide surface of the proximal portion. The actuator spur and the actuator spur receptacle include cooperating surfaces configured to transmit a translational force from the actuator spur to the proximal portion during movement of the actuator spur. The proximal portion includes an over-mold interlock portion that is over-molded onto and non-removably fixed onto the mold-on interlock portion of the distal portion with the plastic material of the proximal portion having an internal female contour and geometry that is married to the contour and geometry of the male mold-on interlock portion of the distal portion of the slide shaft to be non-removably interlocked with the male mold-on interlock portion of the distal portion.

BRIEF DESCRIPTION OF THE DRAWINGS

The foregoing and other features and advantages of the present invention will become apparent to those skilled in the art to which the present invention relates upon reading the following description with reference to the accompanying drawings.

DESCRIPTION OF AN EXAMPLE EMBODIMENT

An example embodiment that incorporates one or more aspects of the invention is described and illustrated in the drawings. The illustrated example is not intended to be a limitation on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Figure 1:
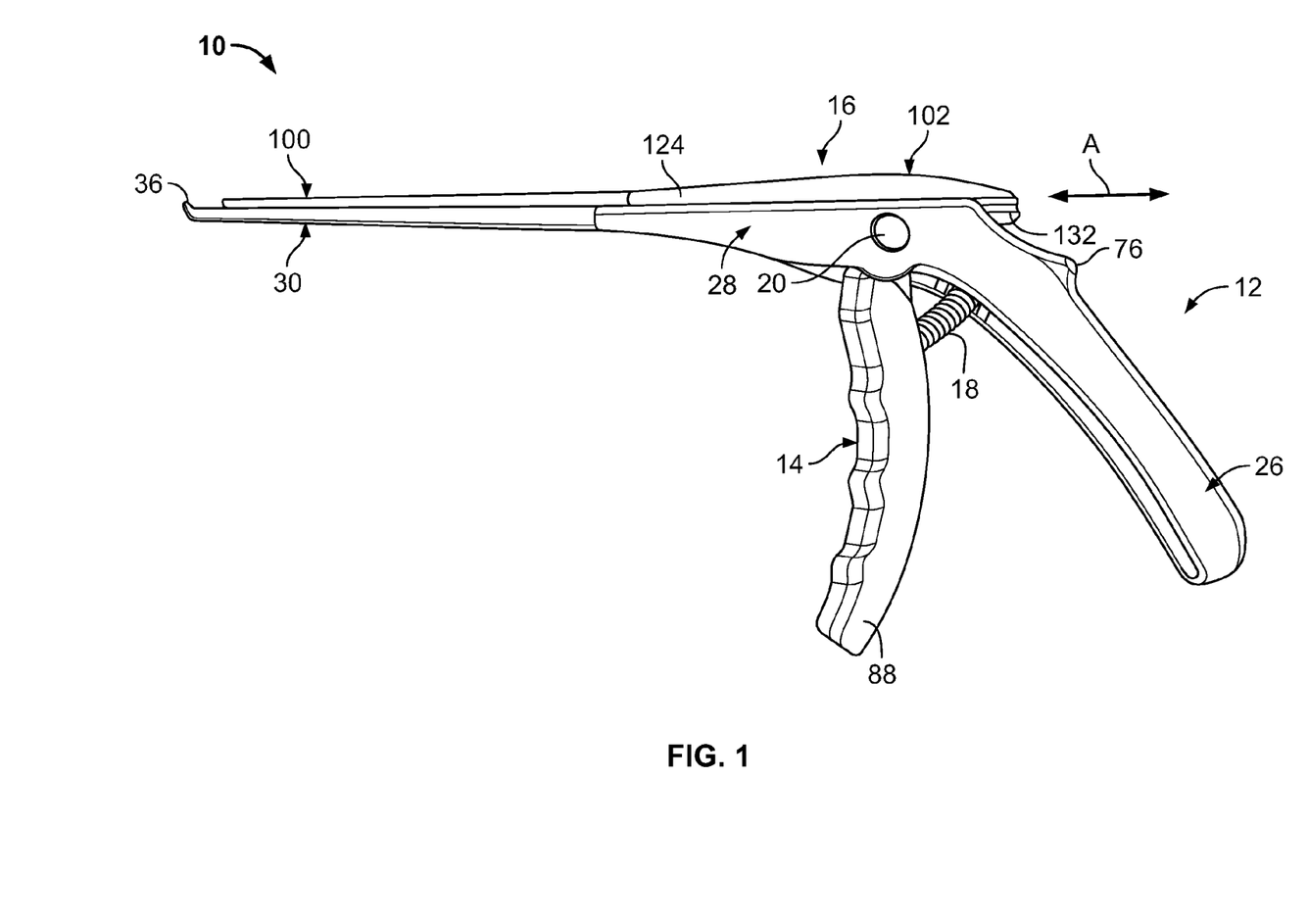
FIG. 1 is an illustration of an example disposable kerrison rongeur in accordance with at least one aspect of the present invention.
Figure 2:
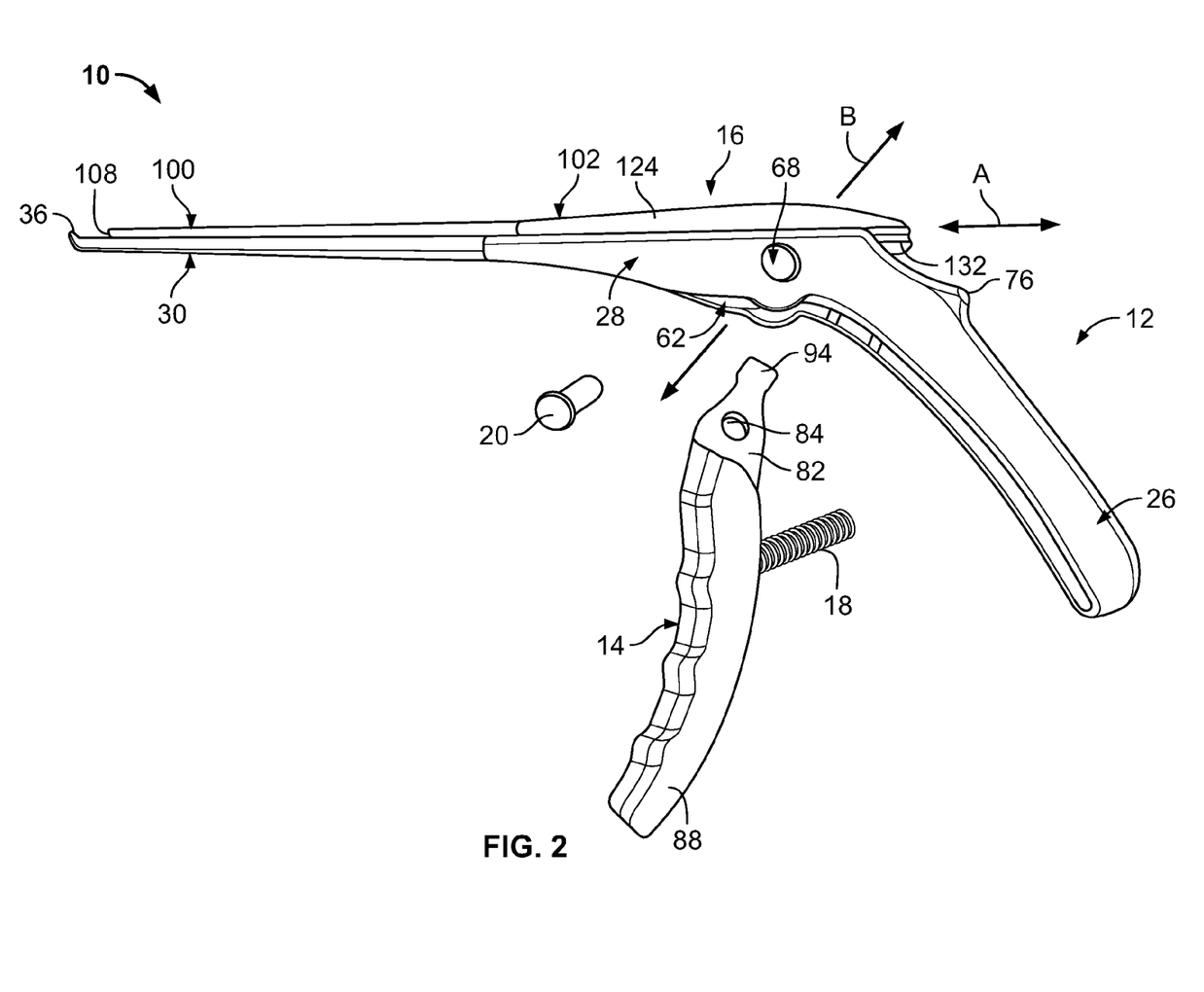
FIG. 2 is a partially exploded illustration of the example disposable kerrison rongeur of FIG. 1.

An example disposable kerrison rongeur 10 in accordance with at least one aspect of the present invention is an illustrated in FIG. 1. The disposable kerrison rongeur 10 is usable by an operator (e.g., a surgeon) for cutting tissue, such as bone, cartilage and the like. The example kerrison rongeur 10 includes the following portions/parts: a base 12, an operable lever 14, a slide shaft 16, a spring 18 and a rivet 20. FIG. 2 shows the lever 14, the spring 18 and the rivet 20 exploded out and away from their normal positions within the disposable kerrison rongeur 10. Only the base 12 and the slide shaft 16 are not exploded away from each other in FIG. 2.

As a general synopsis of operation (FIG. 1), the base 12 and operable lever 14 are grasped by the user (e.g., a surgeon). During use, the slide shaft 16 is moveable relative to the base 12 along an actuation axis A. The movement of the slide shaft 16 relative to the base 12 is cause by operation of the operable lever 14. Specifically, the operable lever 14 is pivoted about the rivet 20, which pivotally supports the lever 14 on the base 12. The spring 18 biases the lever 14 relative to the base 12. This general, synopsis, and the interaction of the base 12, the lever 14 and the slide shaft 16 can be further appreciated via a review of FIG. 3, within which the spring 18 and the rivet 20 are omitted and part of the base 12 is partially section torn away so that the interaction of the base 12, the lever 14 and the slide shaft 16 can be seen.

Some of the inventive aspects of the disposable kerrison rongeur 10 include that the base 12 and the slide shaft 16 are each uniquely constructed/configured to include both metal material and plastic material. Appreciation of this unique construction/configuration can be initiated via the viewing of FIGS. 1-3. The unique construction/configuration to include both metal material and plastic material will be further presented as the example disposable kerrison rongeur 10 is described further following. Also, other inventive aspects will be presented as the example disposable kerrison rongeur 10 is described.

Focusing now upon the base 12 of the example disposable kerrison rongeur 10, the base includes a handle portion 26, a body portion 28 and a shaft portion 30. The shaft portion 30 has a major elongation along the actuation axis A and is made of a metal material. As such, the shaft portion 30 is an elongate, relatively thin and tapering portion of the base 12 of the disposable kerrison rongeur 10. The shaft portion 30 includes a slide support surface 34 (see FIG. 4) that extends along the actuation axis A. It is to be noted that, as viewed within the figures, the actuation axis A can be considered to extend generally horizontally (i.e., generally left/right) in the figures. The slide support surface 34 is flat and smooth and faces upward, in the in the reference frame of the figures.

The remainder of the surface(s) of the shaft portion 30 that extend(s) along the actuation axis A may be of suitable shape and configuration (e.g., rounded and/or piano-curved in cross-section and tapering). Generally, the contour is slimmer than a typical, previously known, kerrison rongeur.

At a distal end (i.e., away from the grasp of the user, generally left in the figures), the shaft portion 30 of the shown example includes a foot portion 36. As mentioned, the foot portion 36 is located at a distal end of the shaft portion 30 and thus the foot portion is at a distal end of the slide support surface 34. The foot portion 36 extends transverse to the actuation axis A. Specifically, the foot portion 36 extends (generally upward in the views of the figures) from the slide support surface 34 at an angle relative to the actuation axis A. The foot portion 36 includes a face 38 against which tissue (e.g., bone, cartilage, etc.) is pressed during a cutting action. The foot portion 36 can have any suitable construction, configuration, etc. to help with the cutting action, such as one or more recesses (example is shown in the figures).

Figure 5:
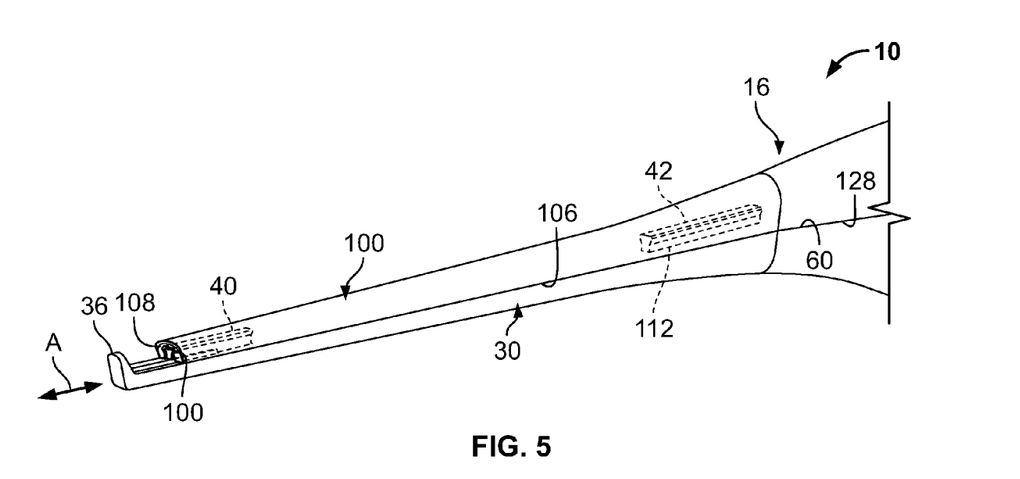
FIG. 5 is a slightly enlarged illustration of a distal half portion of the example disposable kerrison rongeur of FIG. 1, with some portions shown in phantom to allow viewing of underlying, hidden portions.

The shaft portion 30 of the base 12 includes at least one slide guide protrusion (e.g., 40) located along the slide support surface 34 of the shaft portion 30 of the base 12, which extends away from the slide support surface in a direction transverse to the actuation axis (FIG. 5). In the shown example, two slide guide protrusions 40, 42 are located along the slide support surface 34 of the shaft portion 30 of the base 12. A first one of the slide guide protrusions 40 is located near to, but a short distance from, the foot portion 36. Specifically, the first slide guide protrusion 40 is spaced away from the foot 36 a distance to allow tissue (e.g., bone, cartilage) that is to be cut to be within the space between the foot and the first slide guide protrusion. A second one of the slide guide protrusions 42 is located near to an end of the shaft portion 30 opposite to the foot portion 36.

Each slide guide protrusion 40, 42 can have a respective (e.g., different) configuration, construction, shape and/or size. For both of the two slide guide protrusions 40, 42, the respective slide guide protrusion has an extent parallel to the actuation axis A. Also for both of the two slide guide protrusions 40, 42, the respective slide guide protrusion can have a general male dovetail cross-sectional shape for a cross-section taken perpendicular to the actuation axis A. The first slide guide protrusion 40, which is located near the foot portion 36, may have an extended height so that sidewalls of the first slide glide protrusion are parallel for a distance and diverge from each other above that distance to provide a male dovetail (e.g., an overall modified male dovetail) profile (see FIG. 4). The second slide guide protrusion 42, which is located away from the foot portion 36, may have sidewalls that only diverge from each to provide a male dovetail profile (see FIG. 5).

The shaft portion 30 of the base 12 can include a tissue sample rest shelf 46 (see FIG. 4) that is adjacent to the foot portion 36 and slightly raised above the slide support surface 34 of the shaft portion of the base. The first slide guide protrusion 40 can be located adjacent to the tissue sample rest shelf 46 and/or may overlap onto the tissue sample rest shelf.

The shaft portion 30 includes at least one male mold-on interlock portion 50 (see FIG. 3) located at an end of the shaft portion opposite to the foot portion 36. Each male mold-on interlock portion 50 has a contour and geometry configured to non-removably interlock with an over-molded plastic material. With the shown example, one male mold-on interlock portion 50 is provided. Also with the shown example, an example contour and geometry 52 is shown for the male mold-on interlock portion 50. Specifically, the example contour and geometry 52 is such that the male mold-on interlock portion 50 is a projection that extends generally parallel to the actuation axis A and in a direction further away from the foot portion 36. The projection of the male mold-on interlock portion 50 has a cross-sectional area, as taken perpendicular to the actuation axis A, which increases as the projection extends in the direction further away from the foot portion 36. Of course, other contours and/or geometries that are configured to non-removably interlock with an over-molded plastic material are possible.

The body portion 28 of the base 12 is made of the over-molded plastic material that is over-molded onto the at least one male mold-on interlock portion 50 of the shaft portion 30. As such, the body portion 28 of the base 12 includes an over-mold interlock portion 54 that is over-molded onto and non-removably fixed onto the male mold-on interlock portion 50 of the shaft portion 30. The plastic material at the over-mold interlock portion 54 of the body portion 28 has an internal female contour and geometry 56 that is married to the contour and geometry 52 of the male mold-on interlock portion 50 to be non-removably interlocked with the male mold-on interlock portion of the shaft portion 30. In some respects, there is no lost or unused space volume due to the marriage of the female to male contours and geometries 52, 56. As used herein, marriage is defined to mean united intimately with surface(s) touching and following each other's contour and geometry. Moreover, the marriage means that the female to male contours and geometries are connected and thus the body portion 28 of the base 12 is connected to the shaft portion 30 of the base.

The connection between the female to male contours and geometries 52, 56 and thus connection of the body portion 28 of the base 12 to the shaft portion 30 of the base is a fixed, permanent and non-removable connection. As used herein, fixed, permanent and non-removable means that the two portions 28, 30 (i.e., body portion and shaft portion of the base) cannot be removed without destroying the kerrison rongeur 10. This fixed, permanent and non-removable connection is an attendant structural aspect of the plastic over-mold.

Figure 6:
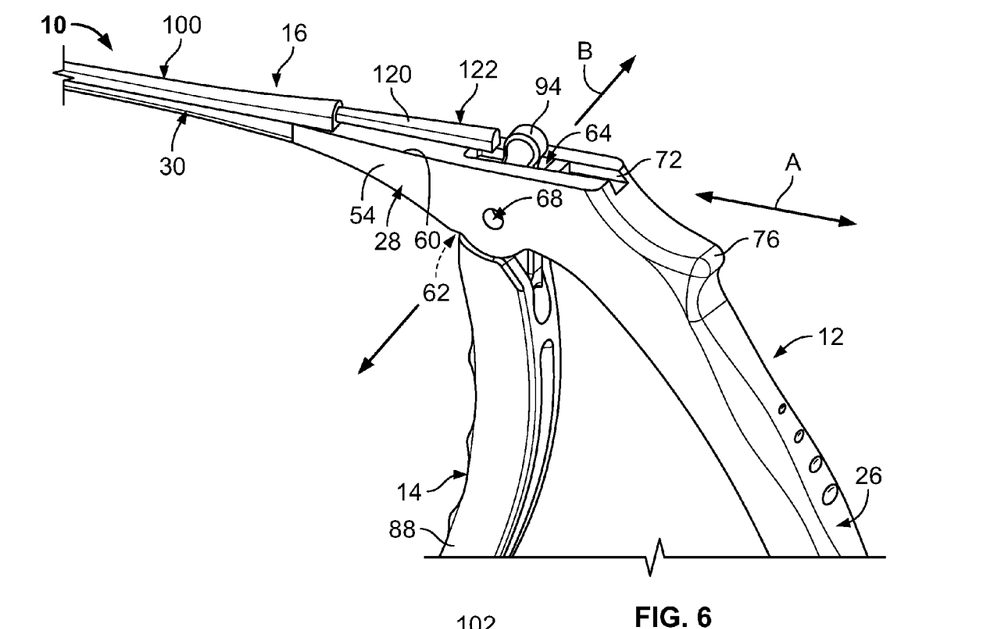
FIG. 6 is an illustration of a proximal half portion of the example disposable kerrison rongeur of FIG. 1, with some portions removed to allow viewing of underlying, hidden portion and with some parts omitted.

The body portion 28 has a major elongation along the actuation axis A. The body portion 28 includes a slide support surface 60 (see FIG. 6) extending along the actuation axis A. The slide support surface 60 of the body portion is coplanar with the slide support surface 34 of the shaft portion 30 of the base 12. A lever passageway 62 extends through the body portion 28 generally transverse to the actuation axis A. The lever passageway 62 extends vertically (as viewed within the figures) from a bottom side of the body portion 28 to a top side of the body portion. As such the lever passageway 62 extends through, and thus has an opening 64 through, the slide support surface 60 of the body portion 28. Moreover, the lever passageway 62 thus provides an open interior volume within the body portion 28. In the shown example, the lever passageway 62 is defined in part by two planar interior surfaces (only one shown in FIG. 3, the other has been torn way) of the body portion 28 of the base 12. The two interior surfaces are parallel to each other. In the reference frame of the figures, the two interior surfaces extend vertically (i.e., as viewed in the figures).

A bearing bore 68 (see FIG. 6) extends through the body portion 28 on a bore axis B. The bore axis B extends transverse to and offset from the actuation axis A. As shown within the figures, the bore axis B can be considered to extend horizontally (e.g., somewhat in/out of the plane of the figures). The bearing bore 68 transversely interests the lever passageway 62. As such, the bearing bore 68 extends through the interior volume provided by the lever passageway 62. With the shown example, the bearing bore 68 has a circular cross-section as taken perpendicular to the bore axis B. It is to be appreciated that the rivet 20 is to be secured into the bearing bore 68. Moreover, the rivet 20 is to be permanently secured into the bearing bore 68 so that the rivet is non-removable (note that FIG. 2 only shows the rivet 20 exploded out for clarity, and does not show a readily removable aspect). As used herein, permanent and non-removable means that the rivet 20 cannot be removed without destroying the kerrison rongeur. This permanent and non-removable placement is an attendant structural aspect of the rivet 20, which is in contrast to a removable screw, which could loosen and become lost.

The body portion 28 of the base 12 includes at least one slide guide receptacle 72 (FIG. 6) located along the slide support surface 60. Within the shown example one slide guide receptacle 72 is provided. The slide guide receptacle 72 extends into the body portion 28 from the slide support surface 60 in a direction (i.e., downward as viewed within the figures) transverse to the actuation axis A. The slide guide receptacle 72 has a general female dovetail shape in cross-section (i.e., transverse to the actuation axis A). Also, the slide guide receptacle 72 may extend to open at an end of the body portion 28 that is furthest from the foot portion 36.

In the shown example, the handle portion 26 of the base 12 is made of the plastic material and extends from the body portion 28 of the base 12 away from the shaft portion 30 of the base and transverse to the actuation axis A. In one specific example, the handle portion 26 of the base 12 and the body portion 28 of the base are integrally/simultaneously molded together as a single piece of the plastic material. Herein, integrally molded means that the handle portion 26 and the body portion 28 are part of one whole singularly formed/molded piece.

It is to be recalled that the handle portion 26 is to be engaged by the user (e.g., surgeon). In one specific example, a palm of the user rests against an outer most (e.g., rightmost as shown in the figures) surface of the handle portion 26. Of course, how the handle portion 26 is engaged by the user can be varied and may be a preference of the user.

It is to be appreciated that the use of plastic material to make the handle portion 26 of the base 12, provides for several structural aspects. One structural aspect is that the size of the handle portion 26 can easily be varied (i.e., modified) without too much variation (i.e., modification) of overall weight. Part of such structural aspect can be provided via the relative lightness of the plastic material (e.g., in comparison to metal material) and/or a use of molded-in voids or hollowness (i.e., the absence of plastic material to provide air volume/space) at some locations. The figures show some example, voids or hollowness. Specifically, a void (e.g., a hollow recess) is present at an inner and lower (as viewed within the figures, as such the left of the handle portion) side of the handle portion 26 (see FIGS. 1-3). Typically, such inner and lower side of the handle portion 26 is often not engaged by the user during use.

Turning back specifically to the structural aspect that the size of the handle portion 26 can be varied (i.e., modified), such variation (i.e., modification) can allow the handle portion, and thus the entire kerrison rongeur 10, to have a more ergonomically designed sizing. In one example, the handle portion 26 can be approximately 20% laterally thicker (i.e., lateral width) than a typical metal kerrison rongeur handle portion.

The handle portion 26 can include a spur 76. The spur 76 may be located at an upper, as viewed within the figures, extent of the handle portion 26. At such location at the upper extent, the spur 76 can rest against a tissue web between thumb and index finger (i.e., purlicue area) of the hand of the user while the user holds the kerrison rongeur 10 during use. However, the user need not hold the kerrison rongeur 10 as such. Thus, the position of the spur 76 can be placed a different location. Moreover, it is to be noted that the spur 76 has a protrusion extent (i.e., the length amount that the spur extends away from the remainder of the handle portion 26). In the figures, the protrusion extent is toward the right. It is to be noted that the protrusion extent is generally lesser than the protrusion extent that is present for spurs on kerrison rongeur made of metal material. It is to be appreciated that it is possible to more easily select sizing and positioning of the spur 76 based upon the plastic material and the attendant width sizing of the handle portion 26, which itself is part of a structural aspect that can be provided via the relative ease of manufacturability and/or lightness of the plastic material.

It should be noted that the location and/or sizing of the spur 76 can allow a greater variety of options (i.e., orientations, positions and the like) for the (e.g., surgeon) to hold the kerrison rongeur 10 during use. For example, the kerrison rongeur 10 could even be held inverted (as compared to the orientation shown within the figures). The smaller spur 76 may be less likely to uncomfortably block/press the hand of the user.

Also, the handle portion 26 may have surface contour(s)/texturing(s). See FIGS. 6 and 7 for examples. Such, surface contouring/texturing can provided for ease of grip-ability, increased resistance to grip slippage (as compared to a lack of surface texturing), etc. It is to be appreciated that it is possible to more easily select sizing, positioning, etc. of the surface contour(s)/texturing(s) based upon the plastic material and the attendant width sizing of the handle portion, which itself is part of a structural aspect that can be provided via the relative ease of manufacturability and/or lightness of the plastic material.

On the inner side of the handle portion 26, a spring pocket 78 (see FIG. 3) is provided. The spring pocket 78 is a recess or void into which a first end portion of the spring 18 is located. As some further explanation of the spring 18, the spring is made of metal material. The spring 18 is a helical coil spring (i.e., helix coil that extends along a spring axis) and is a compression spring in that the spring provides a resistive force against compression of the spring. It should be appreciated that the spring 18 is also capable of lateral (i.e., transverse to the spring axis) movement and resistance to such lateral movement. Such, movement causes the spring 18 to take on an arc shape (see FIG. 1).

The surface(s) of the handle portion 26 that define the spring pocket 78 retain the first end portion of the spring 18 and thus retain the spring. Such retention occurs while at the same time the spring 18 is permitted to operate (i.e., actuate so as to contract and expand in response to application of compressive force and removal of such compressive force, respectively). It is to be noted that the location of the spring pocket 78 of the handle portion 26 is located at an upper (as viewed within the figures) end of the handle portion, at/adjacent to a junction of the handle portion and the body portion 28 of the base 12. Within the shown example, the spring pocket 78 is located generally/roughly opposite to the location of the spur 76 (i.e., in terms of inner and outer surfaces of the handle portion 26). Thus, the spring 18 is located generally at the upper (as viewed within the figures) end of the handle portion 26, at/adjacent to the junction of the handle portion and the body portion 28 of the base 12.

It should be noted that the spring 18 being a helical spring and/or the location of the generally at the upper (as viewed within the figures) end of the handle portion 26, at/adjacent to the junction of the handle portion and the body portion 28 of the base 12 are advantageous structural aspects. Specifically, the helical spring 18, with smooth, curved surface(s) does not have a propensity to cut/pinch a hand of the user (e.g., surgeon). Similarly, the helical spring 18 does not have a propensity to cut/pinch a glove worn upon the hand of the user. Such is in distinction to other types of springs/spring devices, such as scissor-type springs. Such scissor-type springs require attachment to a handle at location(s) further away from a body portion (i.e., much lower as viewed within the figures) than the location of the spring pocket 78.

As indicated previously, the kerrison rongeur 10 includes the operable lever 14. The lever 14 is made of a plastic material. The lever 14 may be made of the same type (e.g., same composition) of plastic material as the handle portion 26 and the body portion 28 of the base 12, or the lever 14 could be made of a different type of plastic material. In terms of operation of the lever 14, the lever is moveable relative to the base 12. The movement of the lever 14 causes the overall operation of the kerrison rongeur 10 as will be appreciated to the person skill in the art and as will be discussed further following.

Figure 3:
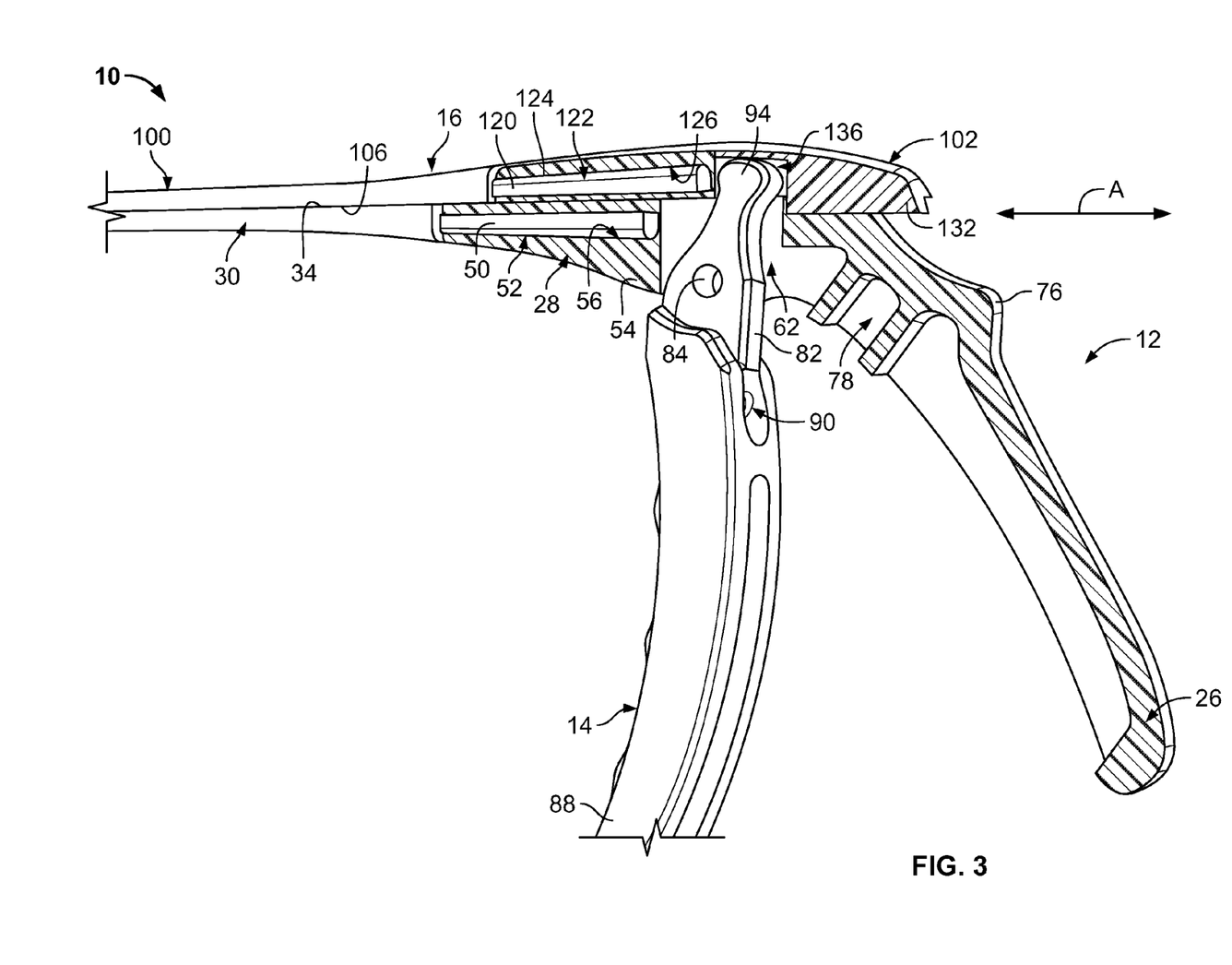
FIG. 3 is a slightly enlarged and partial section torn-away illustration of the example disposable kerrison rongeur of FIG. 1, with some parts omitted.

The lever 14 includes a pivot portion 82 that is located within the lever passageway 62 (see FIG. 3). The pivot portion 82 has a bearing bore 84 that is aligned (i.e., co-axial on the bore axis B) with the bearing bore 68 of the body portion 28 of the base 12. The pivot portion 82 is pivotably movable relative to the body portion 28 on the bore axis B. The pivot portion 82 may have some surfaces that cooperate and/or are counterparts to the surfaces of the body portion 28 of the base 12 that define the lever passageway 62. For example, the pivot portion 82 has two flat and planar surfaces. These two surfaces of the pivot portion 82 are parallel to each other. In the reference frame of the figures, the two flat and planar surfaces extend vertically (as viewed in the figures). Each of these surfaces of the pivot portion 82 is adjacent to a respect one of the flat and planar surfaces of the body portion 28 of the base 12 that define the lever passageway 62.

A handle portion 88 of the lever 14 extends from the pivot portion and away from the body portion transverse to the actuation axis. The handle portion 88 of the lever 14 is movable relative to the handle portion 26 of the base 12 during pivot movement of the pivot portion 82 relative to the body portion 28. The handle portion 88 of the lever 14 is to be engaged by the user (e.g., surgeon). In one specific example, one or more fingers of the user rests against an outer most (e.g., left-most as shown in the figures) surface of the handle portion 88 of the lever. As such, the user can grasp the two handle portions (i.e., of the base and lever). Of course, how the kerrison rongeur 10, and thus the handle portion 88 of the lever 14, is held/engaged by the user can be varied and may be a preference of the user.

It is to be appreciated that the use of plastic material to make the lever 14 provides for several structural aspects. One structural aspect is that the size of the handle portion 88 of the lever 14 can easily be varied (i.e., modified) without too much variation (i.e., modification) of overall weight. Part of such structural aspect can be provided via the relative lightness of the plastic material (e.g., in comparison to metal material) and/or a use of molded-in voids or hollowness (i.e., the absence of plastic material to provide air volume/space) at some locations. The figures show some example voids or hollowness. Specifically, a void (see FIGS. 3, 6 and 7) is present at an inner and lower (as viewed within the figures, as such the right of the handle portion) side of the handle portion 88 of the lever 14. Typically, this side of the handle portion 88 is often not engaged by the user during use.

Turning back specifically to the structural aspect that the size of the handle portion 88 of the lever 14 can be varied (i.e., modified), such variation (i.e., modification) can allow the handle portion of the lever, and thus the entire kerrison rongeur 10, to have a more ergonomically designed sizing. In one example, the handle portion 88 of the lever 14 can be approximately 20% laterally thicker (i.e., lateral width) than a typical metal kerrison rongeur handle portion.

The handle portion 88 can include one or more surface contour(s)/texturing(s). Within the shown example, three lateral projections are provided (see FIGS. 3 and 6). There lateral projections provide finger seating locations there between. Such, surface contouring/texturing can provided for ease of grip-ability, increased resistance to grip slippage (as compared to a lack of surface texturing), etc. It is to be appreciated that it is possible to more easily select sizing, positioning, etc. of the surface contour(s)/texturing(s) based upon the plastic material and the attendant width sizing of the handle portion, which itself is part of a structural aspect that can be provided via the relative ease of manufacturability and/or lightness of the plastic material.

It should be noted that the location and/or sizing of the surface contouring/texturing can allow a greater variety of options (i.e., orientations, positions and the like) for the (e.g., surgeon) to hold the kerrison rongeur 10 during use. For example, the kerrison rongeur 10 could even be held inverted (as compared to the orientation shown within the figures). The surface contouring/texturing may be less likely to uncomfortably block/press the hand of the user and/or provide for better grip-ability within such other hold options.

Figure 7:
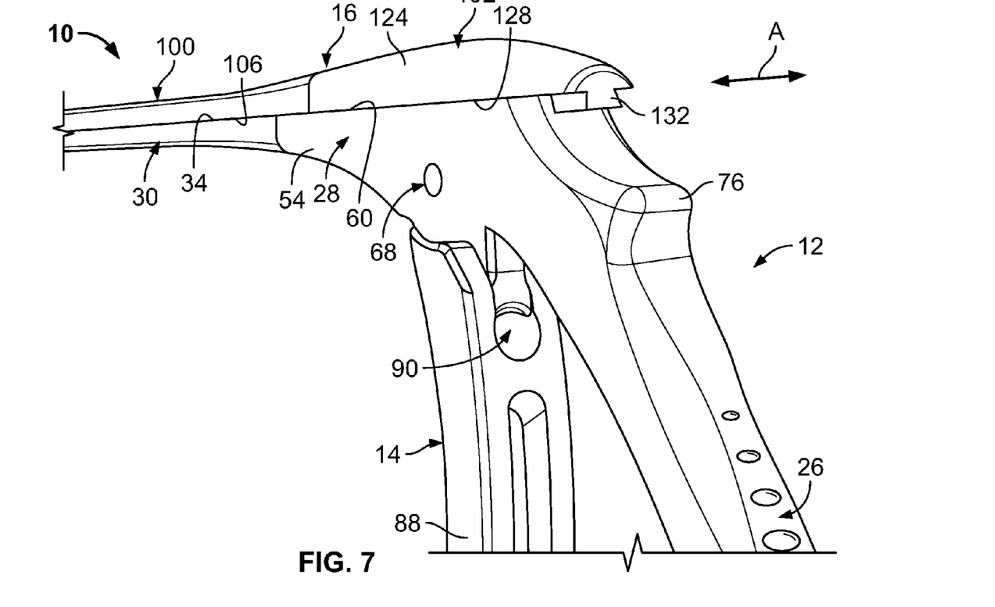
FIG. 7 is an illustration of the proximal half portion of the example disposable kerrison rongeur of FIG. 1 and with some parts omitted.

On the inner side of the handle portion 88 of the lever 14, a spring pocket 90 is provided (see FIGS. 3 and 7). The spring pocket 90 is a recess or void into which a second end portion of the spring 18 is located. The surface(s) of the handle portion 88 of the lever 14 that define the spring pocket 90 retain the second end portion of the spring 18 and thus retain the spring. Such retention occurs while at the same time the spring 18 is permitted to operate (i.e., actuate so as to contract and expand in response to application of compressive force and removal of such compressive force, respectively). It is to be noted that the location of the spring pocket 90 is located at an upper (as viewed within the figures) end of the handle portion 88 of the lever 14. The location of the spring pocket 90 is at/adjacent to a junction of the handle portion 88 and the pivot portion 82 of the lever 14. Within the shown example, the spring pocket 90 on the lever 14 is located generally/roughly opposed to the location of the spring pocket 78 on the handle portion 26 of the base 12. Thus, the spring 18 is located generally at the upper (as viewed within the figures) end of the area between the two handle portions 26, 88.

As mentioned, there are advantageous structural aspects associated with such location of the spring 18. Recall that some of the example advantageous structural aspects include no propensity to cut/pinch a hand of the user (e.g., surgeon) and/or no propensity to cut/pinch a glove worn upon the hand of the user.

An actuator spur (see FIGS. 2, 3 and 6) of the lever 14 extends from the pivot portion 82 at an end of the lever that is opposite to the handle portion 88 of the lever 14. As viewed within the figures, the actuator spur 94 thus extends upward from the pivot portion 82. The actuator spur 94 extends out, past the opening 64 through the slide support surface 60 of the body portion 28 of the base 12. The actuator spur 94 thus extends away from the body portion 28 and transverse to the actuation axis A. Within the shown example, the actuator spur 94 has a rounded or bulbous profile as viewed from the side (i.e., viewed into the plane of the figures).

The actuator spur 94 is movable relative to the body portion 28 of the base 12 during pivot movement of the pivot portion 82 relative to the body portion 28. The movement of the actuator spur 94 includes a translational movement component along the actuation axis A. As such, the movement of the actuator spur 94 includes a fore and aft movement with reference to the base 12 along the actuation axis A.

The slide shaft 16 of the kerrison rongeur 10 has a major elongation along the actuation axis A. The slide shaft 16 includes a distal portion 100 and a proximal portion 102 (see FIGS. 1 and 2). With regard to the slide shaft 16, the distal portion 100 is furthest (i.e., distal) from the hand of the user while the user grasps the two handle portions 26, 88. As such, the proximal portion 102 is nearest (i.e., proximal) to the hand of the user while the user grasps the two handle portions 26, 88. As will be discussed further following, and as the name implies, the slide shaft 16 is slidably movable relative to the base 12.

Focusing upon the distal portion 100 (see FIG. 5), the distal portion itself has a major elongation along the actuation axis and is made of a metal material. The distal portion 100 is an elongate, relatively thin and tapering portion of the slide shaft 16 of the kerrison rongeur 10. A slide surface 106 (see FIGS. 3-5) of the distal portion 100 extends along the actuation axis A and is supported upon at least the slide support surface 34 of the shaft portion 30 of the base 12. The slide surface 106 is flat and smooth, and faces downward in the view of the figures. As will be discussed further following, the slide surface 106 slides upon the at least the slide support surface 34 of the shaft portion 30 of the base 12 during movement of the slide shaft 16 relative to the base. The remainder of the surface(s) of the distal portion 100 that extend(s) along the actuation axis A may be of suitable shape and configuration (e.g., rounded and/or piano-curved in cross-section and tapering). Generally, the contour is slimmer than a typical kerrison rongeur.

Figure 4:
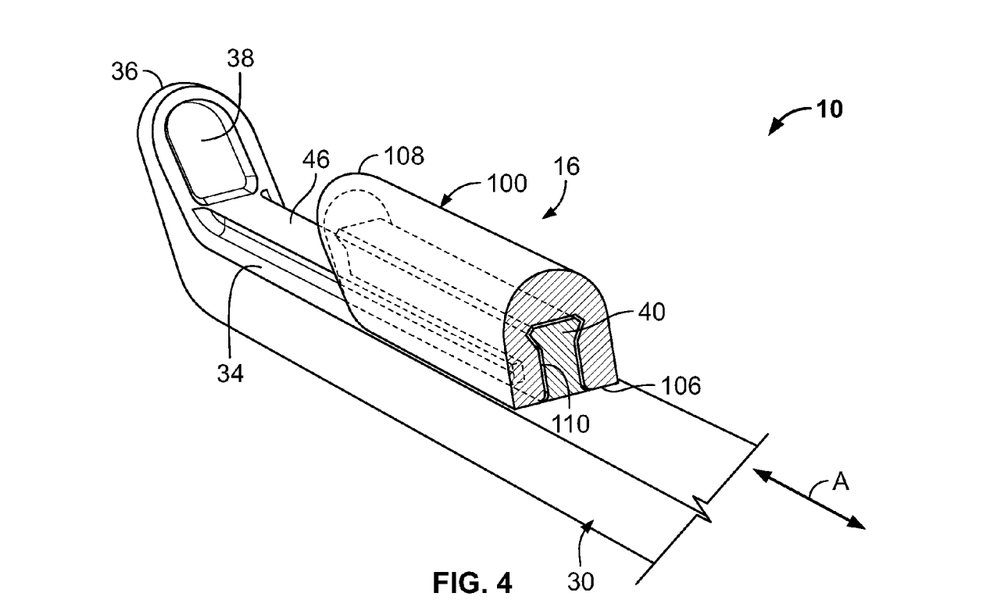
FIG. 4 is a further enlarged and partial section torn-away illustration of a distal end of the example disposable kerrison rongeur of FIG. 1, with some portions shown in phantom to allow viewing of underlying, hidden portions.

At a furthest end (i.e., away from the grasp of the user), the distal portion 100 of the shown example includes a cutting edge 108 located to be opposed to the foot portion 36 (see FIG. 4). In general, the shape of the cutting edge 108 is complementary (i.e., mating) to the foot portion 36. Also, adjacent to the cutting edge 108, the distal portion 100 is hollow. The cutting edge 108 is movable toward the foot portion 36 to cut tissue located between the cutting edge 108 and the foot portion 36 during the movement of the slide shaft 16 in a cutting stroke, which is a movement toward the left as viewed within the figures. It is to be appreciated that as the cutting edge 108 moves to cut, the cut tissue is over-shrouded by the distal portion 100, with the cut tissue being within the hollow of the distal portion and resting upon the tissue sample rest shelf 46. Thus the cut tissue is held by and within the distal portion 100. The cut tissue is unshrouded and thus removable from the kerrison rongeur 10 as the slide shaft 16, and specifically the cutting edge 108, moves back away from the foot portion 36 on the base 12. This can be considered to be a return motion by the slide shaft 16.

The distal portion 100 of the slide shaft 16 includes at least one slide guide receptacle 110 (see FIGS. 4 and 5) located along the slide surface 106. Within the shown example two slide guide receptacles 110, 112 (see FIG. 5) are provided. Each slide guide receptacle 110, 112 extends into the distal portion 100 from the slide surface 106 in a direction transverse to the actuation axis A. A respective one of the slide guide protrusions (e.g., 40) of the shaft portion 30 of the base 12 is located within a respective one of slide guide receptacles (e.g., 110) of the distal portion 100 of the slide shaft 16. Each respective slide guide protrusion 40, 42 of the shaft portion 30 of the base 12 and the respective slide guide receptacle 110, 112 of the distal portion 100 of the slide shaft 16 include complementary and engaging surfaces that are configured to permit the sliding of the slide surface 106 of the distal portion of the slide shaft upon the at least the slide support surface 34 of the shaft portion of the base during movement of the slide shaft relative to the base and configured to prohibit a removal movement of the slide shaft from the base in a direction transverse to the actuation axis A. As such, the surface(s) that define each slide guide receptacle 110, 112 are a female counterpart of the respective dovetail shape of the respective slide guide protrusion 40, 42.

The distal portion 100 of the slide shaft 16 includes at least one male mold-on interlock portion 120 (see FIGS. 3 and 6) located at an end of the distal portion opposite to the cutting edge 108. Each male mold-on interlock portion 120 and has a contour and geometry 122 configured to non-removably interlock with an over-molded plastic material. With the shown example, one male mold-on interlock portion 120 is provided. Also with the figures, an example contour and geometry 122 is shown. Specifically, the example contour and geometry 122 includes a projection that extends generally parallel to the actuation axis A and in a direction further away from the cutting edge 108. The projection of the male mold-on interlock portion 120 has a cross-sectional area, as taken perpendicular to the actuation axis A, which increases as the projection extends in the direction further away from the cutting edge 108. Of course, other contours and/or geometries that are configured to non-removably interlock with an over-molded plastic material are possible.

The proximal portion 102 of the slide shaft 16 is made of the over-molded plastic material that is over-molded onto the at least one male mold-on interlock portion 120 of the distal portion. As such the proximal portion 102 of the slide shaft 16 includes an over-mold interlock portion that is over-molded onto and non-removably fixed onto the mold-on interlock portion 120 of the distal portion 100. The plastic material at the over-mold interlock portion 124 of the proximal portion 102 has an internal female contour and geometry 126 that is married to the contour and geometry 122 of the male mold-on interlock portion 120 to be non-removably interlocked with the male mold-on interlock portion of the distal portion 100. In some respects, there is no lost or unused space volume due to the marriage of the male to female contours and geometries 122, 126. As used herein, marriage is defined to mean united intimately with surface(s) touching and following each other's contour and geometry. Moreover, the marriage means that the male to female contours and geometries 122, 126 are connected and thus the distal portion 100 of the slide shaft 16 is connected to the proximal portion 102 of the slide shaft.

The connection between the male to female contours and geometries 122, 126 and thus connection of the distal portion 100 to the proximal portion 102 is a fixed, permanent and non-removable connection. As used herein, fixed, permanent and non-removable means that the two portions (i.e., distal and proximate portions) cannot be removed without destroying the kerrison rongeur 10. This fixed, permanent and non-removable connection is an attendant structural aspect of the over-mold.

The proximal portion 102 of the slide shaft 16 has a major elongation along the actuation axis A. The proximal portion 102 includes a slide surface 128 extending along the actuation axis A. The slide surface 128 of the proximal portion 102 is coplanar with the slide surface 106 of the distal portion 100 of the slide shaft 16. The slide surface 128 of the proximal portion 102 of the slide shaft 16 slides upon the at least the slide support surface 60 of the body portion 28 of the base 12 during movement of the slide shaft 16 relative to the base. Other surface(s) of the proximal portion that extend(s) along the actuation axis A may be of suitable shape and configuration (e.g., rounded and/or piano-curved in cross-section and tapering).

The proximal portion 102 of the slide shaft 16 includes at least one slide guide protrusion 132 (see FIG. 7) located along the slide surface 128 of the proximal portion 102 and extending away from the slide surface 128 in a direction (i.e., downward) transverse to the actuation axis A. In the shown example, a single slide guide protrusion 132 is located along the slide surface 128 of the proximal portion 102. The slide guide protrusion 132 of the proximal portion 102 is located within the slide guide receptacle 72 of the body portion 28 of the base 12. The slide guide protrusion 132 of the proximal portion 102 of the slide shaft 16 and the respective slide guide receptacle 72 of the body portion 28 of the base 12 include complementary and engaging surfaces that are configured to permit the sliding of the slide surface 128 of the proximal portion 102 of the slide shaft 16 upon the at least the slide support surface 60 of the body portion 28 of the base 12 during movement of the slide shaft 16 relative to the base and configured to prohibit a removal movement of the slide shaft from the base in a direction transverse to the actuation axis A. As such, the surface(s) that define the slide guide receptacle 72 is a female counterpart of the respective dovetail shape of the slide guide protrusion 132.

An actuator spur receptacle 136 (see FIG. 3) extends into the proximal portion 102 from the slide surface 128 (e.g., from bottom as viewed within the figures) of the proximal portion and generally transverse to the actuation axis A. The actuator spur receptacle 136 only extends partially into the proximal portion 102 and does not penetrate completely through the proximal portion. In the shown example, the actuator spur receptacle 136 is defined in part by two flat and planar interior surfaces (only one shown in FIG. 3, the other has been torn off) of the proximal portion 102 of the slide shaft 16. The two interior surfaces are parallel to each other. In the reference frame of the figures, the two interior surfaces extend vertically (as viewed in the figures). Also, the actuator spur receptacle 136 is also defined in part by fore and aft interior surfaces of the proximal portion of the slide shaft. These fore and aft interior surfaces may be planar or curved.

The actuator spur 94 is located within the actuator spur receptacle 136. As mentioned, the actuator spur 94 is movable fore and aft with reference to the base 12 along the actuation axis A. The actuator spur 94 and the actuator spur receptacle 136 include cooperating surfaces configured to transmit a translational force from the actuator spur 94 to the proximal portion 102 during movement of the actuator spur. Within the shown example, the actuator spur 94 presses upon the fore surface within the actuator spur receptacle 136 when the handle portion 88 of the lever 14 is moved toward the handle portion 26 of the base 12 (i.e., the two handle portions are squeezed together against the bias of the spring 18). Such bearing of the actuator spur 94 upon the fore surface within the actuator spur receptacle 136 causes the slide shaft 16 to move (i.e., toward the left as viewed within the figures) along the actuation axis A such that the cutting edge 108 is moved toward the foot portion 36. Also within the shown example, the actuator spur 94 presses upon the aft surface within the actuator spur receptacle 136 when pressure upon the handle portion 88 of the lever 14 is released and the handle portion of the lever moves way from the handle portion 26 of the base 12 (i.e., the two handle portions are moved away from each other via the bias of the spring 18). Such bearing of the actuator spur 94 upon the aft surface within the actuator spur 94 receptacle causes the slide shaft 16 to move (i.e., toward the right as viewed within the figures) along the actuation axis A such that the cutting edge 108 is moved away from the foot portion 36.

The disclosed subject matter has been described with reference to the example embodiments described above. Modifications and alterations will occur to others upon a reading and understanding of this specification. Example embodiments incorporating one or more aspects of the invention are intended to include all such modifications and alterations.

The invention claimed is:

1. A disposable kerrison rongeur for cutting tissue, the kerrison rongeur comprising:
　a base, the base comprising:
　　a handle portion, a body portion and a shaft portion;
　　the shaft portion having a major elongation along an actuation axis and being made of a metal material, the shaft portion comprising:
　　　a slide support surface extending along the actuation axis;
　　　a foot portion located at a distal end of the slide support surface and extending transverse to the actuation axis; and
　　　a male mold-on interlock portion located at an end of the shaft portion opposite to the foot portion and having a contour and geometry configured to non-removably interlock with an over-molded plastic material;
　　the body portion having a major elongation along the actuation axis and being made of the over-molded plastic material, the body portion comprising:
　　　an over-mold interlock portion that is over-molded onto and non-removably fixed onto the mold-on interlock portion of the shaft portion with the plastic material having an internal female contour and geometry that is married to the contour and geometry of the male mold-on interlock portion to be non-removably interlocked with the male mold-on interlock portion of the shaft portion;
　　　a slide support surface extending along the actuation axis, the slide support surface of the body portion being coplanar with the slide surface support of the shaft portion;
　　　a lever passageway extending through the body portion and having an opening through the slide support surface of the body portion; and a bearing bore extending through the body portion on a bore axis, the bearing bore transversely intersecting the lever passageway; and the handle portion being made of the over-molded plastic material and extending from the body portion of the base away from the shaft portion of the base and transverse to the actuation axis;

an operable lever made of a plastic material and moveable relative to the base, the lever comprising:

a pivot portion located within the lever passageway, the pivot portion having a bearing bore that is aligned with the bearing bore of the body portion, the pivot portion is pivotably movable relative to the body portion on the bore axis;

a handle portion extending from the pivot portion and away from the body portion transverse to the actuation axis, the handle portion of the lever being movable relative to the handle portion of the base during pivot movement of the pivot portion relative to the body portion; and an actuator spur extending from the pivot portion past the opening through the slide support surface of the body portion, away from the body portion and transverse to the actuation axis, the actuator spur being movable relative to the body portion of the base during pivot movement of the pivot portion relative to the body portion, the movement of the actuator spur including a translational movement component along the actuation axis;

a slide shaft having a major elongation along the actuation axis and being moveable relative to the base along the actuation axis, the slide shaft comprising:

a distal portion and a proximal portion;

the distal portion being made of a metal material, the distal portion comprising:

a slide surface extending along the actuation axis and supported upon at least the slide support surface of the shaft portion of the base, the slide surface slides upon at least the slide support surface of the shaft portion of the base during movement of the slide shaft relative to the base;

a cutting edge located to be opposed to the foot, the cutting edge being movable toward the foot to cut tissue located between the cutting edge and the foot; and a male mold-on interlock portion located at an end of the distal portion opposite to the cutting edge and having a contour and geometry configured to non-removably interlock with an over-molded plastic material;

the proximal portion being made of a plastic material, the proximal portion comprising:

a slide surface extending along the actuation axis and supported upon at least the slide support surface of the body portion of the base, the slide surface of the proximal portion of the slide shaft slides upon at least the slide support surface of the body portion of the base during movement of the slide shaft relative to the base;

an actuator spur receptacle extending into the proximal portion from the slide surface of the proximal portion, the actuator spur and the actuator spur receptacle include cooperating surfaces configured to transmit a translational force from the actuator spur to the proximal portion during movement of the actuator spur; and an over-mold interlock portion that is over-molded onto and non-removably fixed onto the mold-on interlock portion of the distal portion with the plastic material of the proximal portion having an internal female contour and geometry that is married to the contour and geometry of the male mold-on interlock portion of the distal portion of the slide shaft to be non-removably interlocked with the male mold-on interlock portion of the distal portion.

2. The disposable kerrison rongeur as set forth in claim 1, wherein the shaft portion of the base further comprising a slide guide protrusion, which is made of metal material, located along the slide support surface of the shaft portion of the base and extending away from the slide support surface in a direction transverse to the actuation axis, the distal portion of the slide shaft further comprising a slide guide receptacle located along the slide surface of the distal portion and extending into the distal portion from the slide surface of the distal portion in a direction transverse to the actuation axis, the slide guide protrusion of the shaft portion of the base is located within the slide guide receptacle of the distal portion of the slide shaft, the slide guide protrusion of the shaft portion of the base and the slide guide receptacle of the distal portion of the slide shaft include complementary and engaging surfaces that are configured to permit the sliding of the slide surface of the distal portion of the slide shaft upon at least the slide support surface of the shaft portion of the base during movement of the slide shaft relative to the base and configured to prohibit a removal movement of the slide shaft from the base in a direction transverse to the actuation axis.

3. The disposable kerrison rongeur as set forth in claim 1, wherein the proximal portion of the slide shaft further comprising a slide guide protrusion, which is made of metal material, located along the slide surface of the proximal portion of the slide shaft and extending away from the slide surface of the proximal portion in a direction transverse to the actuation axis, the body portion of the base further comprising: a slide guide receptacle located along the slide support surface of the body portion of the base and extending into the body portion of the base from the slide surface of the body portion in a direction transverse to the actuation axis, the slide guide protrusion of the slide shaft is located within the slide guide receptacle of the body portion of the base, the slide guide protrusion of the slide shaft and the slide guide receptacle of the body portion of the base include complementary and engaging surface that are configured to permit the sliding of the slide surface of the slide shaft upon at least the slide support surface of the body portion of the base during movement of the slide shaft relative to the base and configured to prohibit a removal movement of the slide shaft from the base in a direction transverse to the actuation axis.

4. The disposable kerrison rongeur as set forth in claim 1, wherein the handle portion of the base is constructed to include molded-in hollowness.

5. The disposable kerrison rongeur as set forth in claim 1, wherein the handle portion of the lever is constructed to include molded-in hollowness.

6. The disposable kerrison rongeur as set forth in claim 1, further including a spring configured to bias movement of the lever relative to the base.

7. The disposable kerrison rongeur as set forth in claim 6, wherein the spring is configured as a helix coil spring.

8. The disposable kerrison rongeur as set forth in claim 7, wherein the handle portion of the base is constructed to include a spring pocket into which one end portion of the spring is located.

9. The disposable kerrison rongeur as set forth in claim 8, wherein the spring pocket of the handle portion is located adjacent to a junction of the handle portion and the body portion of the base.

10. The disposable kerrison rongeur as set forth in claim 7, wherein the handle portion of the lever is constructed to include a spring pocket into which one end portion of the spring is located.

11. The disposable kerrison rongeur as set forth in claim 10, wherein the spring pocket of the handle portion is located adjacent to a junction of the handle portion and the pivot portion of the lever.

12. The disposable kerrison rongeur as set forth in claim 1, further including a rivet pivotally and permanently securing the pivot portion of the lever to the body portion of the base.

13. The disposable kerrison rongeur as set forth in claim 1, wherein the proximal portion of the slide shaft further comprising a slide guide protrusion, which is made of plastic material, located along the slide surface of the proximal portion of the slide shaft and extending away from the slide surface in a direction transverse to the actuation axis, the body portion of the base further comprising a slide guide receptacle located along the slide support surface of the body portion and extending into the body portion from the slide support surface of the body portion in a direction transverse to the actuation axis, the slide guide protrusion of the proximal portion of the slide shaft is located within the slide guide receptacle of the body portion of the base, the slide guide protrusion of the proximal portion of the slide shaft and the slide guide receptacle of the body portion of the base include complementary and engaging surfaces that are configured to permit the sliding of the slide surface of the proximal portion of the slide shaft upon at least the slide support surface of the body portion of the base during movement of the slide shaft relative to the base and configured to prohibit a removal movement of the slide shaft from the base in a direction transverse to the actuation axis.

14. The disposable kerrison rongeur as set forth in claim 1, wherein the handle portion of the base is molded to have surface texturing of plastic material.

15. The disposable kerrison rongeur as set forth in claim 1, wherein the handle portion of the lever is molded to have surface texturing of plastic material.

\* \* \* \* \*